United States Patent
Wang (10) Patent No.: US 6,974,964 B1
(45) Date of Patent: Dec. 13, 2005

(54) METHOD AND APPARATUS FOR THREE-DIMENSIONAL SURFACE SCANNING AND MEASUREMENT OF A MOVING OBJECT

(76) Inventor: Bu-Chin Wang, 12231 Kirkdale Dr., Saratoga, CA (US) 95070

( * ) Notice: Subject to any disclaimer, the term of this patent is extended or adjusted under 35 U.S.C. 154(b) by 207 days.

(21) Appl. No.: 10/460,582

(22) Filed: Jun. 11, 2003

Related U.S. Application Data (60) Provisional application No. 60/389,169, filed on Jun. 17, 2002.

(51) Int. Cl.[7] .......................... G01N 21/86; G01V 8/00
(52) U.S. Cl. ........................... 250/559.29; 250/559.22; 345/419; 345/426; 345/427; 345/629; 345/581; 702/95; 702/152; 382/154
(58) Field of Search ...................... 250/559.29, 559.22; 382/184; 348/66; 702/94–95, 152–153; 345/419, 345/426–427, 581, 586, 629–630; 433/29; 356/602–608

(56) References Cited

U.S. PATENT DOCUMENTS

| | | | | |
|---|---|---|---|---|
| 5,754,680 A | * | 5/1998 | Sato et al. ................... | 382/154 |
| 6,044,170 A | * | 3/2000 | Migdal et al. .............. | 382/154 |
| 6,064,759 A | * | 5/2000 | Buckley et al. ............. | 382/154 |
| 6,476,812 B1 | * | 11/2002 | Yoshigahara et al. ....... | 345/427 |
| 2003/0204364 A1 | * | 10/2003 | Goodwin et al. ........... | 702/152 |

* cited by examiner

*Primary Examiner*—Stephone B. Allen
*Assistant Examiner*—Suezu Ellis
(74) *Attorney, Agent, or Firm*—The Kline Law Firm (57) ABSTRACT

An apparatus and method to scan and collect data relative to the position of a moving object. The method includes the calibration, equations, and algorithm needed to compute the surface coordinates of an object. The preferred embodiment of the apparatus includes two light sources and four area array image sensors, one moving device, and one computing device. The device scans the object, generates data, computes the position, and provides a complete measure of the 3D surface coordinates of an object. The methodology includes calibration of a known pattern to the area array image sensor, equations to map the physical points to the image sensor, algorithms to determine a best estimate of the coordinates of occluded points, and techniques to merge the computed coordinates from different sections of the object.

11 Claims, 14 Drawing Sheets

METHOD AND APPARATUS FOR THREE-DIMENSIONAL SURFACE SCANNING AND MEASUREMENT OF A MOVING OBJECT

This application claims the benefit of U.S. Provisional Application No. 60/389,169, filed Jun. 17, 2002.

BACKGROUND OF THE INVENTION

1. Field of the Invention

The present invention relates to a method and apparatus for the measurement of three-dimensional surface coordinates of an object with controlled movement along a slit line. More particularly the present invention provides an improved method of computing the coordinates of a line-scan based object.

2. Description of the Prior Art

The prior art has several examples of devices that utilize a light stripe and image sensors to obtain the coordinates of a subject object. The conventional triangulation computation is a cost effective method. Several references disclose methodologies using triangulation to compute the coordinates of an object. The triangulation methods become cost effective and highly precise when implemented with a PC. One example of such a prior art reference is the "Method and Apparatus for Measuring Profile of Three-Dimensional Object", of Yukio Sato et al, U.S. Pat. No. 4,794,262, issued Dec. 27, 1988. Another is the "XYZ Coordinates Measuring System" of Osamu Ozeki, Kazunori Higuchi, and Shin Yamamoto, U.S. Pat. No. 4,961,155, issued Oct. 2, 1990. Still another triangulation based method is described in "A Simple Method for Range Finding Via Laser Triangulation", by Hoa G. Nguyen and Michael R. Blackburn, published in January, 1995, as NraD technical document 2734. An example of a current art product utilizing a triangulation method is the IVP Ranger SAH5, by IVP Integrated Products, Inc.

In conventional triangulation methods, the use of the focus length of the image sensor must be used in the computation of the position of the subject object. Since the focus length is small relative to the distance from the sensor to the object, the measured value of the focus length significantly affects the accuracy of the computation.

Accordingly, it is an object of the present invention to provide a computation method which is independent of the focus length, thereby improving the accuracy of the position computation.

It is another object of the present invention to provide a new technique to improve the surface scan capability on various objects. A light source and an image sensor (collectively referred to as a scan module) are used in conventional triangulation-based methods. However, the current art devices available on the market are limited, typically in one of two ways: (1) The scan module itself is typically a stand alone item, such as the LD100*-*F and the LD250*-*F Laser Distance Meters manufactured by the Toshiba Corporation, and the device disclosed in "A Laser Range Scanner Designed for Minimum Calibration Complexity", by James Davis and Xing Chen in the 2001 IEEE Proceedings of the $3^{rd}$ International Conference on Digital Imaging and Modeling. (2) Multiple scan modules are utilized, but each scan module operates independently of the others. Devices employing this scheme are exemplified by the KLS 51 and KLS 171 Laser Sensors from Kreon Technologies. The present invention employs multiple scan modules aligned together to jointly scan the object and produce the combined line based coordinates. Using this arrangement, more accurate measurement results and reduced occlusion can be achieved.

SUMMARY OF THE INVENTION

The present invention is a combination of algorithms and an apparatus to measure the surface coordinates of a three dimensional (3D) object. A unique algorithm, which provides mathematical equations and calibration techniques to compute the coordinates, is described. The apparatus includes a moving device to move the subject object, two set of scan modules, and a computer. Each scan module consists of a light source and at least two area image sensors. The two aligned modules scan the moving object at a constant speed. As the object is scanned, each data point is used to compute coordinates, which are then merged to form one line of data. Upon completion of the moving object scan, all the individual sliced line data is compiled to form the surface coordinates of the 3D object.

An advantage of the present invention is that a unique set of equations and calibration techniques are used to compute the surface coordinates of a 3D object. The equations are independent from the focus length of the image sensor, thereby eliminating the sensitivity of the accuracy of the computation due to any inaccuracy in measurement of the focus length inherent in most existing scanners. The calibration techniques make the coordinate computation insensitive to the distance from sensor to the coordinate origin.

Another advantage of the present invention is that a second scan module is used to scan the 3D object under the same planar light, thereby increasing the area available to scan for image data, which of course improves the accuracy of the measurement.

A still further advantage of the present invention is that it merges two sets of independently measured slice based coordinate data and then forms the complete 3D composite data. This method reduces alignment error and provides more accurate coordinates of the 3D object surface.

These and other objects and advantages of the present invention will become apparent to those skilled in the art in view of the description of the best presently known mode of carrying out the invention as described herein and as illustrated in the drawings.

DETAILED DESCRIPTION OF THE INVENTION

The present invention is a three dimensional (3D) scanning technique based on a non-contact device, the scan module. The scan module utilizes a line light source and an image sensor to scan the surface of a physical object. A set of mathematical equations are used to compute the coordinates defining the scanned object's surface. Multiple aligned scan modules are used, with the data from the multiple scan modules being merged into a single coordinate map.

Figure 1:
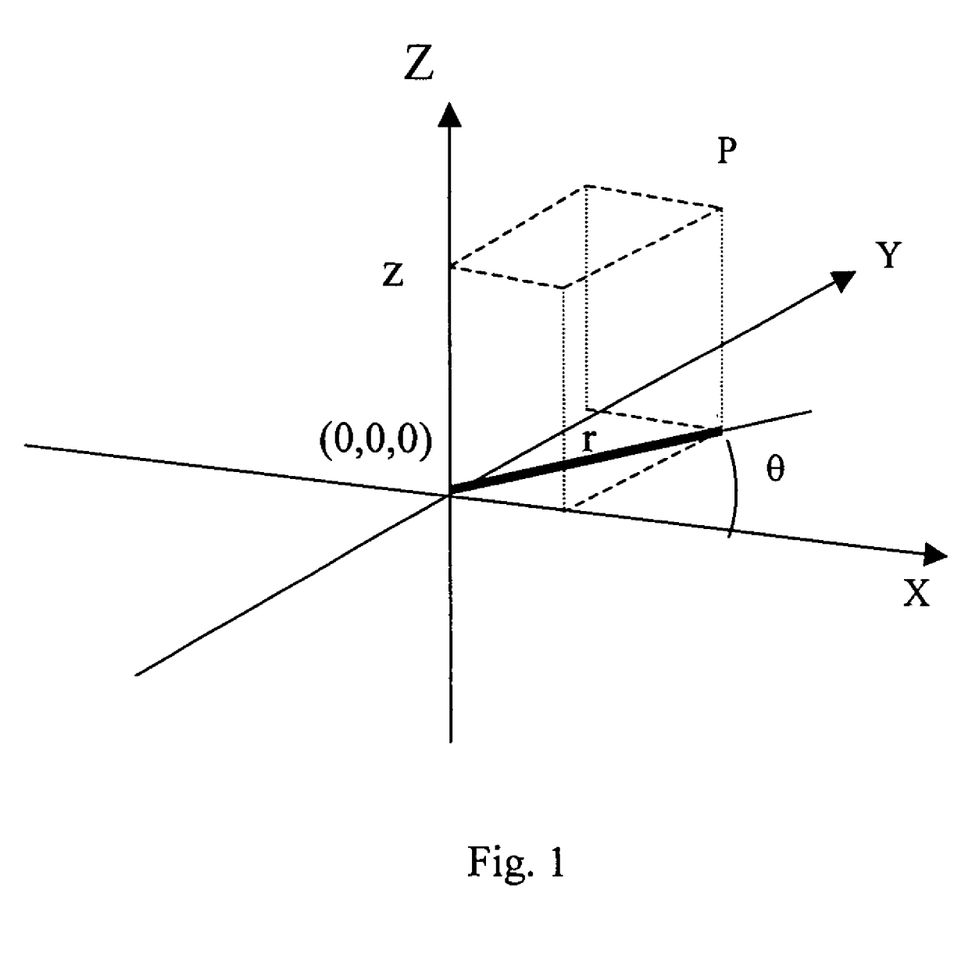
FIG. 1 illustrates a rectangular and cylindrical coordinate system.

The position of a point P can be represented by either rectangular coordinates (x, y, z), or by cylindrical coordinates (r, θ, z). FIG. 1 displays the relationship of these two systems.

$$x = r^* \cos \theta$$

$$y = r^* \sin \theta$$

z is the same in both systems

Figure 2:
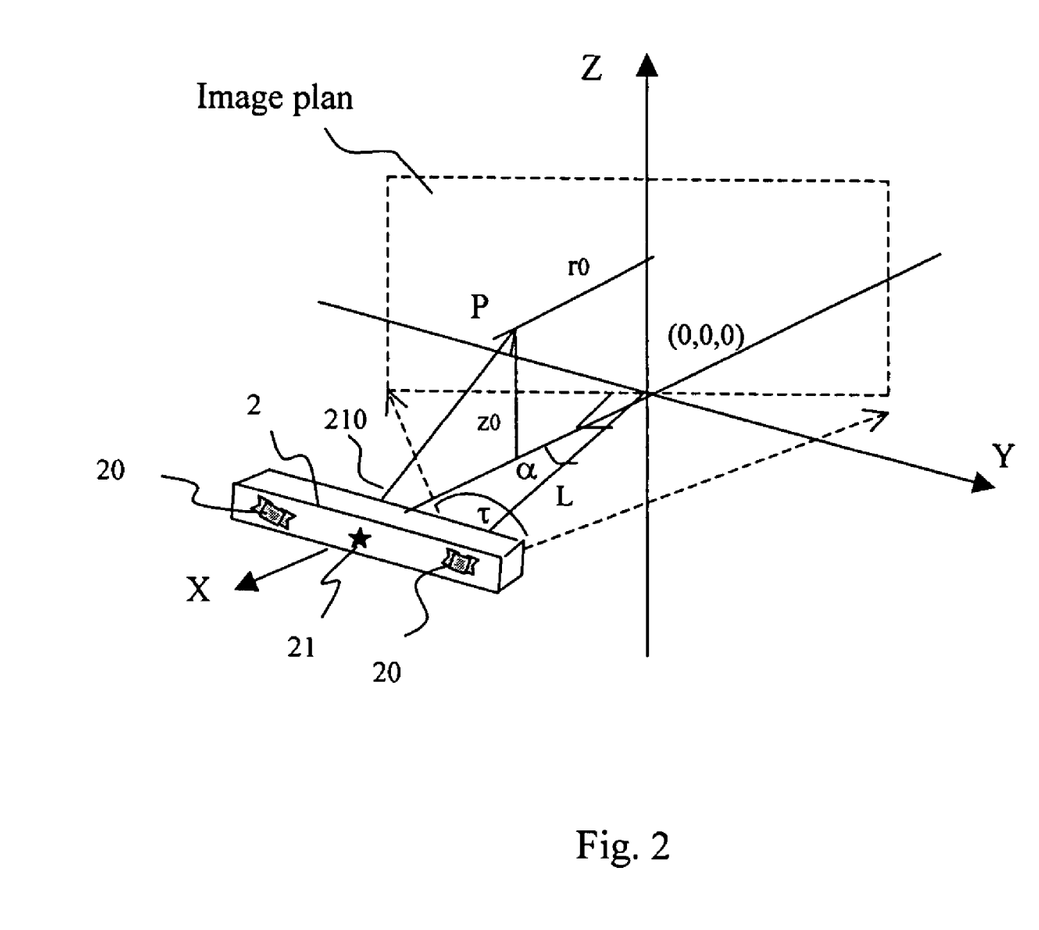
FIG. 2 shows a new stripe light based scanning system.

There exist many light based techniques to measure the coordinates defining the surface of an object. FIG. 2 illustrates the measuring system of the present invention comprising a scan module 2 which includes a light source 21, an image sensor 20, a projected light stripe 210 (that travels from light source 21 to P), and a corresponding image plane. The parameters required to compute the coordinates of a scanned object are listed below:

P is a point of an object with an unknown position and coordinates $(r_0, \theta, z_0)$.

The image sensor 20, (which is a camera or the equivalent), is situated on the XY plane and faces the origin and the Z-axis. Two image sensors 20 are utilized in this first preferred embodiment of the present invention.

L is the distance between the image sensor 20 and the origin.

α is an angle between the image sensor 20 and light source 21 (or the X-axis). α is greater than 0° but less than 90°. (The smaller the angle, the less accurate the resulting coordinate computation, but the greater the area that can be scanned.)

The light source 21, which is typically a laser, is located on the X-axis. The light source 21 projects toward the origin and the Z-axis. The light source 21 is a stripe, planar, or sheet line generator.

τ is the angle of the "Field of View" of the image sensor 20. This value limits the viewing angle of image sensor 20. Objects whose size exceeds the viewing angle of image sensor 20 cannot be completely detected by image sensor 20.

The light source 21 and the image sensor 20 are packaged together as a scan module 2. The scan module 2 will typically comprise at least two image sensors 20, spaced equidistantly at the sides of the light source 21. The distance between the two image sensors 20 is dependent upon the angle α and the value L, namely 2L sin α.

Figure 3:
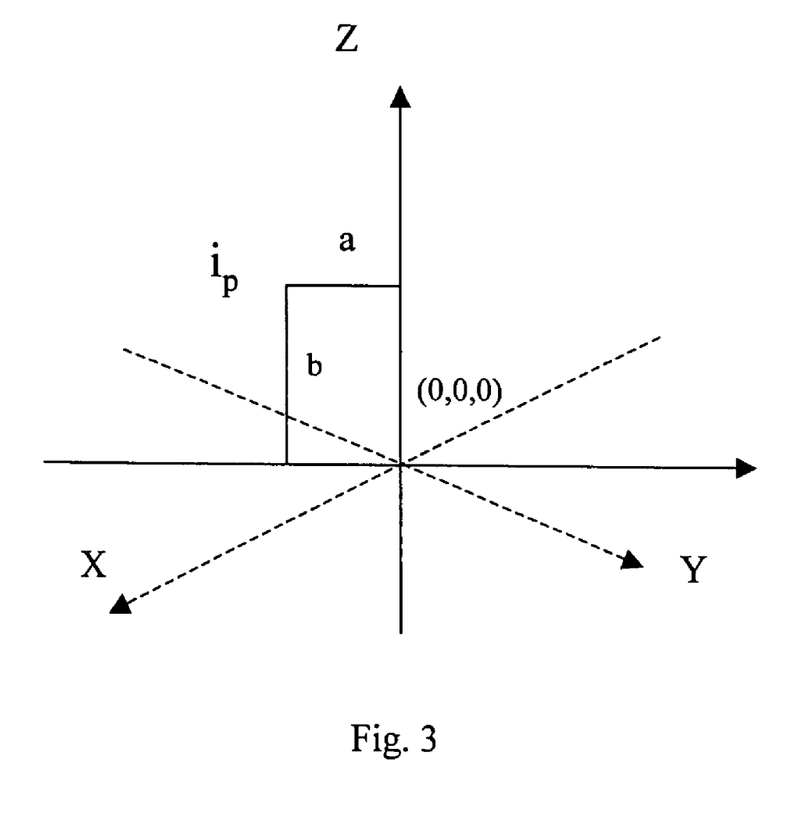
FIG. 3 displays a camera image of point $i_p$.

FIG. 3 shows the image sensor image $i_p$ of point P upon being illuminated by light source 21 and mapped onto the image plane. The distances of $i_p$ from the vertical Z-axis and the horizontal axis are "a" and "b" respectively.

Figure 4A:
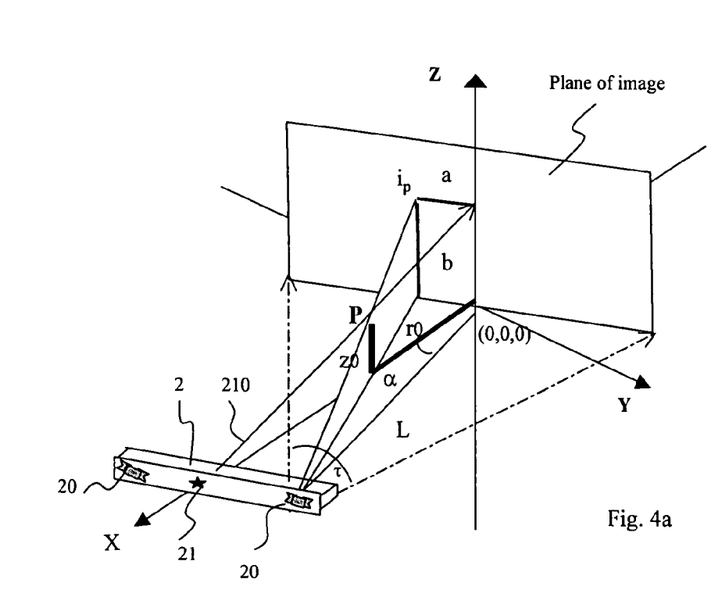
FIG. 4a is a perspective view of point P located in front of the origin, and its projected image $i_p$.
Figure 4B:
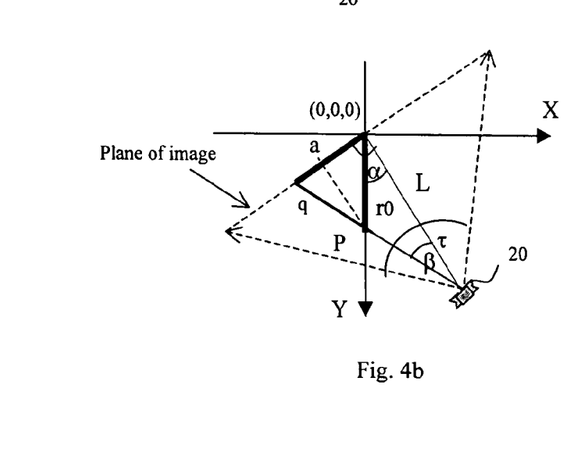
FIG. 4b is a top view from the Z-axis of point P.

It is clear that L and a are preset and known values, while "a" and "b" must be measured from the image plane. Given L, α, a, and b, the coordinates of P can be computed as illustrated in FIG. 4a, which shows a point P with coordinates $(r_0, z_0)$ to be determined in a cylindrical coordinate system. The light stripe 210 generated by the light source 21 maps the point P onto the image sensor image plane as the point $i_p$. The values "a" and "b" are the horizontal distance of $i_p$ from the Z-axis and vertical distance of $i_p$ from the X-Y plane respectively. By looking down from the Z-axis to the X-Y plane, as shown in FIG. 4b, one obtains the following relationship:

$$\tan (\alpha+\beta) = (L \sin \alpha)/(L \cos \alpha - r_0)$$

$$r_0 = L \cos \alpha - (L \sin \alpha)/\tan (\alpha,\beta) \quad \text{(Equation 1)}$$

Where the angle β is computed by tan β=a/L.

Figure 4C:
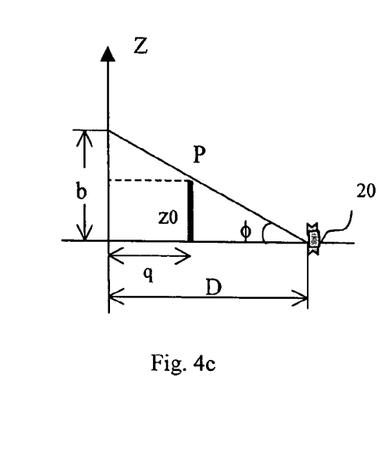
FIG. 4c is a side view of point P.

Viewing the point P from a vantage point perpendicular to the plane containing point P and image sensor 20, the side view of P shown in FIG. 4c is obtained. From both FIG. 4b and FIG. 4c, with "q" as the distance between point P to the image plane as shown in FIG. 4b, one obtains the following:

$$D = \text{SQRT} (L^2 + a^2)$$

$$q = r_0^* \sin (\pi/2 - \alpha)/\sin (\pi/2 - \beta)$$

$$= r_0 \cos \alpha / \cos \beta$$

$$\tan \phi = b/D$$

$$\tan \phi = z_0/(D-q)$$

$$z_0 = (D-q) \cdot b/D \quad \text{(Equation 2)}$$

From Equations 1 & 2, $r_0$ and $z_0$ (the cylindrical coordinates of P) can be derived. The corresponding rectangular coordinates are, $$x = r_0 \cos\theta; \quad y = r_0 \sin\theta; \quad z = z_0$$

Other points on the same line as P and lighted by the stripe 210 from the light source 21 can be computed to obtain their r and z values. By taking line images with an incremental ΔΘ (either counterclockwise or clockwise with respect to the Z-axis), one can obtain a series of line images. Each line image represents one line of scanned data. After a 360° rotation, a complete set of 3D "points of cloud" data are obtained, which can then be processed to model a 3D object.

Figure 5A:
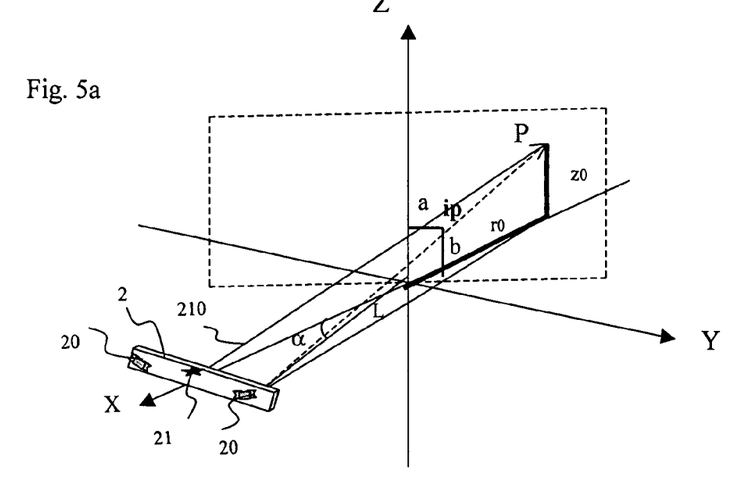
FIG. 5a is a perspective view of P from behind the origin and the projected image $i_p$ of point P.
Figure 5B:
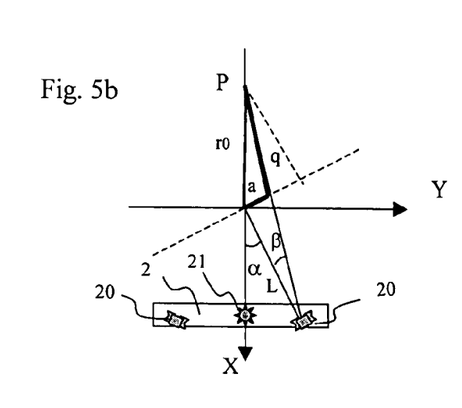
FIG. 5b is a top view from the Z-axis of point P.
Figure 5C:
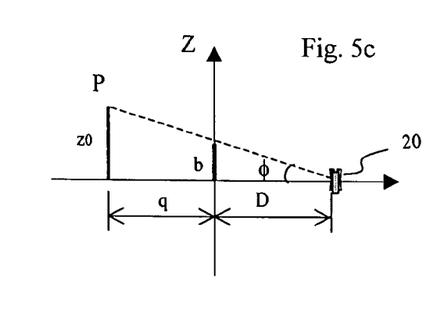
FIG. 5c is a side view of P.

It is possible that an object may have a concave surface. In this case, point P is located "behind" the origin. FIG. 5a shows the image sensor image $i_p$ of a point P behind the origin. Point P has cylindrical coordinates $(r_0, z_0)$. The mapped image $i_p$ of point P has distances from the vertical axis and the horizontal axis "a" and "b" respectively. FIG. 5b displays the top view looking down at point P through the Z-axis. FIG. 5c displays the side view looking at point P from a point perpendicular to the plane containing point P and image sensor 20. Given L, α, a, and b, the 3D coordinates of P can be obtained as shown below:

$$\tan \beta = a/L$$

$$\tan (\alpha-\beta) = L \sin a/(r_0 + L \cos \alpha)$$

$$r_0 = -L \cos \alpha + L \sin \alpha/\tan (\alpha-\beta) \quad \text{(Equation 3)}$$

From FIGS. 5b and 5c, with "q" as the distance between point P to the image plane, $$D = \sqrt{L^2 + a^2}$$

$$q = r_0 - \sin(\pi/2 - \alpha)/\sin(\pi/2 - \beta)$$

$$= r_0 * \cos\alpha/\cos\beta$$

$$\tan\phi = b/D$$

$$\tan\phi = z_0/(q+D)$$

$$z_0 = (q+D)*b/D \quad \text{(Equation 4)}$$

From Equations 3 & 4, one obtains the values of $r_0$ and $z_0$, the cylindrical coordinates of P.

The corresponding rectangular coordinates are, $$x = r_0\cos\theta; \; y = r_0\sin\theta; \; z = z_0$$

Other points on the same line as P and lighted by the source 21 can be computed to obtain their r and z values accordingly. By taking line images with incremental $\Delta\theta$, (either clockwise or counterclockwise with respect to the Z-axis), one can obtain a series of line images. Each image represents one line of scanned data.

As can be seen from both FIGS. 4 and 5, one can apply Equations 1 and 2 to compute the coordinates of an object surface if the image is located to the left side of the origin. Equations 3 & 4 are used when the image is located to the right side of the origin. Notice that this assumes that the image sensor 21 is located to the right side of light source 20 as shown in FIGS. 4 and 5. For an apparatus with the image sensor 20 at the left side of light source 21, the above statement is reversed, that is, Equations 1 and 2 are used for an object to the right side of the origin, and Equations 3 and 4 are used for an object to the left side of the origin.

After a 360° rotation, the complete 3D coordinates (points of cloud) data are obtained, which can then be processed to model a 3D object 4.

Figure 6:
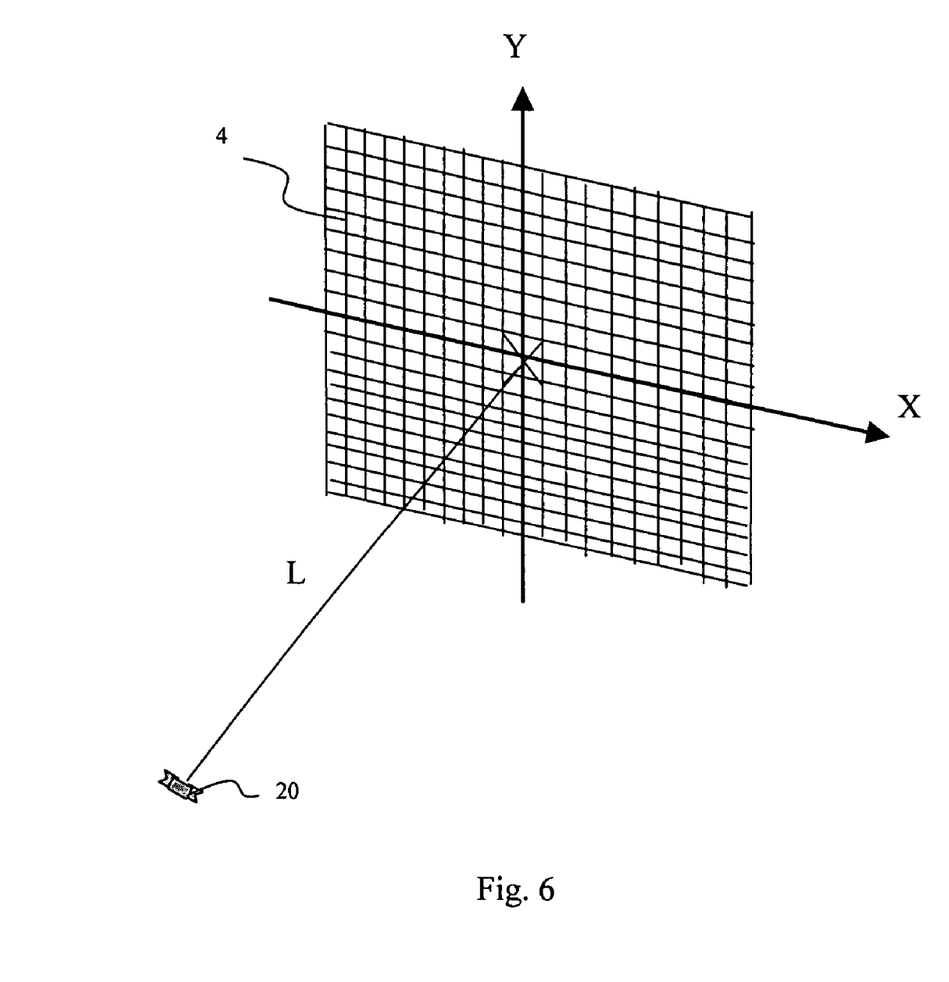
FIG. 6 shows a 20×20 square diagram spaced a distance L from an image sensor.

To obtain the true values of "a" and "b", a test pattern for a given distance L is used to calibrate the image sensor 20. A diagram with a 20×20 grid of squares, each square measuring 1 cm×1 cm, is used as the test pattern. The image sensor 20 is positioned at a fixed distance L from the center of the diagram, as shown in FIG. 6. A photo image read from the image sensor 20 establishes the location of the image $i_p$ corresponding to the point P. Since the size of each of the squares in the diagram is 1 cm×1 cm, the true value of (a, b) can be measured. Applying the values of a and b to Equations 1 and 2 (or 3 and 4), the $r_0$ and $z_0$ values can then be obtained.

Figure 7:
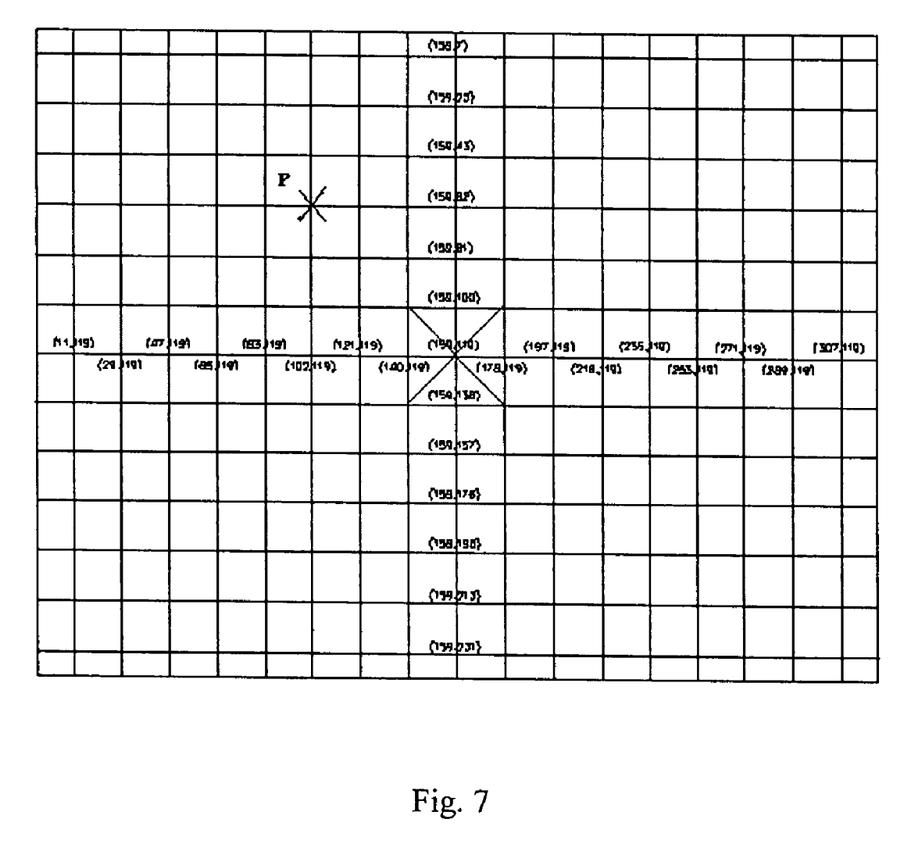
FIG. 7 displays the image of a square diagram mapped to a 320×240 image sensor.

FIG. 7 shows an example of the square diagram based on an image sensor 20 having 320×240 pixels, with $\alpha = 30°$ and distance L=24 cm. As can be seen from this example, the 1 cm true size of the test pattern corresponds to 19 pixels, and the point P in FIG. 7 (marked as an X) corresponds to a=57 pixels or 3 cm, and b=57 pixels or 3 cm. Accordingly, by applying Equations 1 & 2, one obtains $r_0$=4.932 cm, and $z_0$= 2.466 cm.

The previous discussion applies to a setup with object 4 located completely above the X-Y plane where the scan module is located. In the case where the object is located both above and below the X-Y plane, the lighted object is split into two parts—one above the X-Y plane and the other below the X-Y plane. The computation of coordinates for the portion of the object above the X-Y plane is identical to that described above. The computation of coordinates for the portion of the object below the X-Y plane is computed in nearly the same manner, with the exception being that the $z_0$ value is negative. This leads to the final results including coordinates with both positive and negative Z values. Certainly, the scanning setup can be modified so that the entire object to be scanned is above the X-Y plane. The advantage of having portions of the object both above and below the X-Y plane is that the area of the object that cannot be scanned is reduced, as compared to the amount of area that cannot be scanned with the object located only above the X-Y plane.

Once the surface of an object is well defined in terms of its 3D coordinates, in either the cylindrical or rectangular system, the object can then be further processed for various applications. When scanning the surface of an object with a random shape, the conventional method of using only one scan module may well leave a significant area that cannot be scanned. The setup of a scanning system with multiple scan modules capable of scanning top, front, and even inner surface of an object will next be considered.

Figure 8A:
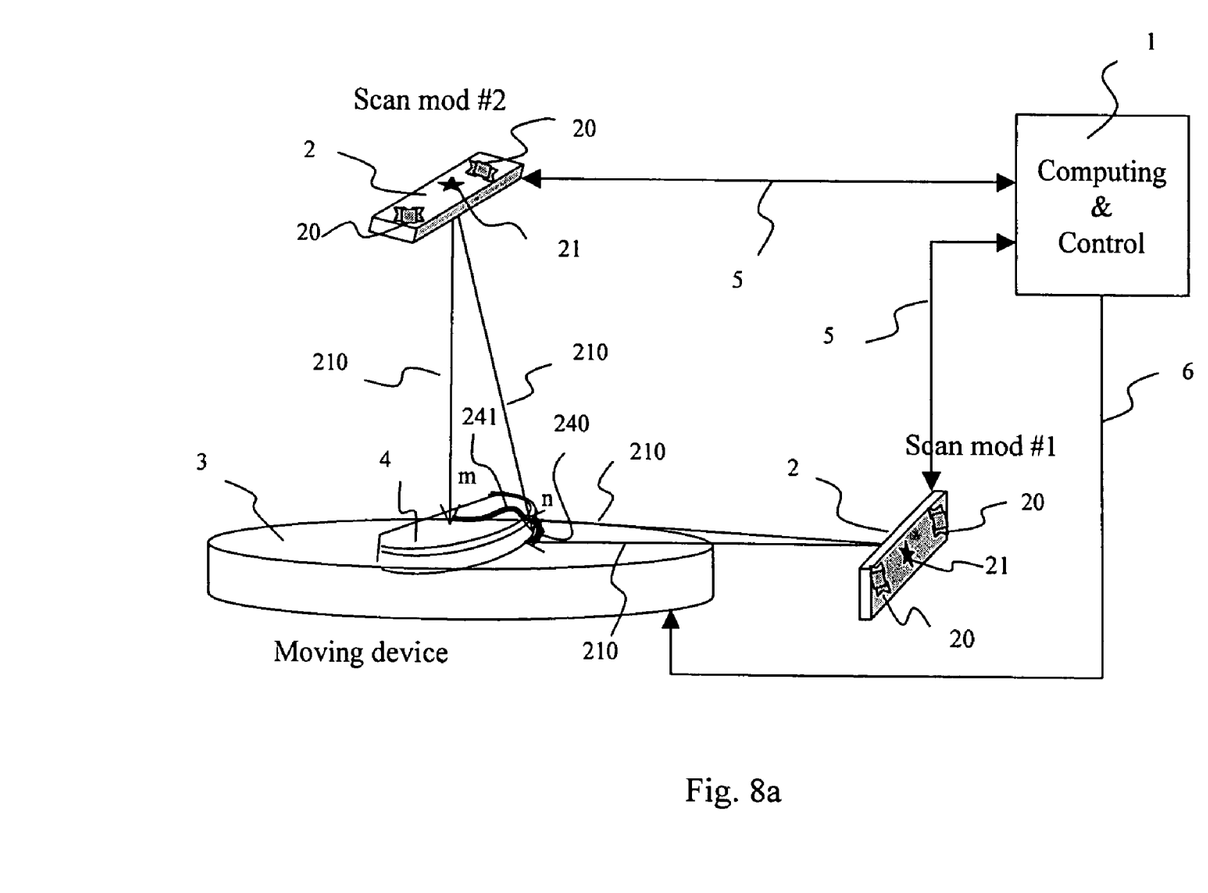
FIG. 8a is a schematic representation of the apparatus for a three dimensional surface scan of the present invention.

FIG. 8a displays a scanning setup comprising two units of the scan module 2, a moving device 3 (which in the preferred embodiment is a turntable), and one computing and control device 1. The object 4 to be scanned is placed on top of the turntable 3. A wiring set 5 provides the two way data and control signal connections between the computing and control device 1 and the scan modules 2, while wiring 6 provides the two way data and control signal connections between the computing device 1 and the moving device 3.

Figure 8B:
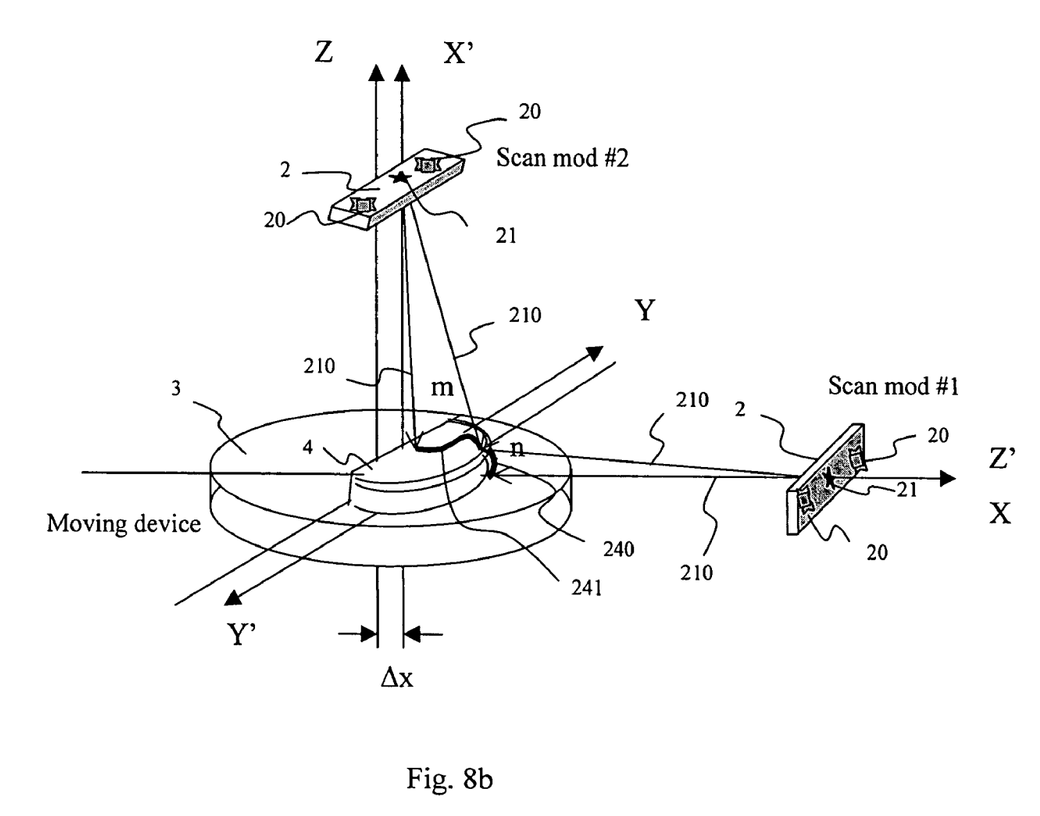
FIG. 8b shows the axes defined by the apparatus with dual scan modules.

FIG. 8b shows a more detailed diagram of the multiple scan module setup with two coordinate systems illustrated. The first coordinate system is related to the first scan module 2 (designated scan mod # 1 in the drawings), which is used to scan the front side of the object 4. The second coordinate system is related to the second scan module 2 (designated scan mod # 2 in the drawings), which is used to scan the top side of the object 4. The center of origin at the intersection of the X, Y, and Z axes refers to the front scan from the first scan module 2. The center of origin at the intersection of the X', Y', and Z' axes refers to the top scan taken by the second scan module 2. The planes containing the two scan modules 2 will typically intersect at a 90° angle. The second scan module 2 is mounted so that different angles can be utilized to maximize the viewing area of object 4 by the image sensors 20. When the second module 2 is not positioned at a 90° angle to the first module 2, the scanned data of the second scan module 2 must undergo a coordinate rotation to properly align with the X-Y-Z system as shown in FIG. 8b for the data merge process. The second scan module 2 scans the entire top surface of object 4. The origin of the X'-Y'-Z' system is $\Delta x$ away from that of the X-Y-Z system. Note that the three axes align with each other: Z' with X, Y' with Y but opposite in orientation, and X' with Z. Conversion between the two systems is therefore straightforward.

The curved segments "m" and "n" in FIGS. 8a & 8b correspond to the two line-light images 241 & 240 that are viewed by the top & front image sensors 20 respectively. The line-light image 241 relates to the top surface of the object 4, and the line-light image 240 relates to the front surface of the object 4. The two line-light images 240 & 241 must be aligned and stay in the same plane, namely the X-Z or X'-Z' plane.

There are two units of the image sensor 20 and one light source 21 in each scanner module 2. The first scan module 2 utilizes equations (1) and (2) to scan and compute the line-based coordinates of the front surface of object 4 through the following steps:

1. The two image sensors 20, located one to each side of the light source 21, are directed toward, and at a distance L away from, the origin of the X-Y-Z system.
2. The two image sensors 20 each have an angle relative to their corresponding light source 21. The line light 210 illuminates the front surface of the object 4.
3. The "b" values from the images of the two image sensors 20 are measured. The two values are identical if the two image sensors 20 are precisely aligned, and no obstacle is located between the image sensors 20. If a minor difference exists, then an average value can be chosen. If one value is missing, then the remaining value is used. If the two values vary too widely, the data is tagged with a maximum value for an optimization process to be performed later in the process.
4. The measurements of the "a" value are identical to "b", but differ in sign, from each of the two image sensors 20. Notice that from Equations 1 and 2, the sign of "a" does not effect the coordinate computation. The steps described above in 3 can be taken to optimize the "a" values.
5. Applying Equations 1 and 2 with given L, α, a, and b, one obtains the position of point P ($r_0$, $z_0$).
6. Repeating the above steps 3 to 5 for every measured "a" and "b", the position of points on the object lighted can be computed as a curved line.

The second scan module 2 is used to scan the top surface of object 4. The two image sensors 20 are directed toward, and at a distance L' away from, the origin of the X'-Y'-Z' system. Each image sensor 20 has an a' angle relative to the light source 21.

The line light 210 is directed at the top surface of the object 4. Steps equivalent to those described for the first scan module 2 are taken to obtain curvature line data based on the X'-Y'-Z' system used for the second scan module 2.

To merge, compose, and optimize the line-based data obtained from the first and second scan modules 20, the following steps are taken:
1. The top scan line-based data from the X'-Y'-Z' system is converted to the X-Y-Z system as shown in FIG. 8b.
2. The points overlapping both the X-axis and Z-axis from the two sets of line-based data are identified.
3. The two sets of overlapping point data are identical if the two scan modules 2 were precisely aligned, and no missing data exists in either set of data. If a minor difference exists, then an average value is chosen. If one data is missing or at its maximum, then the other data point is retained. If the two values vary too widely, the data is tagged with a maximum value for an optimization process to be performed later in the process.
4. The principles of comparison and interpolation described earlier with reference to FIG. 8 can be applied to the overlapping data, the results of which serve as the basis to compose and merge the two independently computed data sets.

Once the new line data is completed, the moving device 3 should move the object to the next position and continue line data generation until the entire scan (360° in circular motion) is completed.

Given the entire set of 3D scanned line data, the following steps are used to generate and optimize the 3D coordinate data:
1. The line-based data with maximum value, which were tagged as erroneous data, is identified.
2. The tagged data is compared with adjacent line-based data, both horizontally and vertically. An interpolated value based on conventional interpolation techniques is obtained. If immediately adjacent line-based data also appears to be in error, more line-based data is used for interpolation.
3. The line-based data is converted to 3D data by taking the small incremental movement of the moving device 3 into consideration. Such as Δθ in circular movement, and $\theta_n = (n-1) \times \Delta\theta$ for the $n^{th}$ line-based data set in the cylindrical coordinate system.
4. After all the line-based data is processed, the new 3D data set is ready and can be transformed into whichever coordinate system, cylindrical or rectangular, is desired.

Figure 9A:
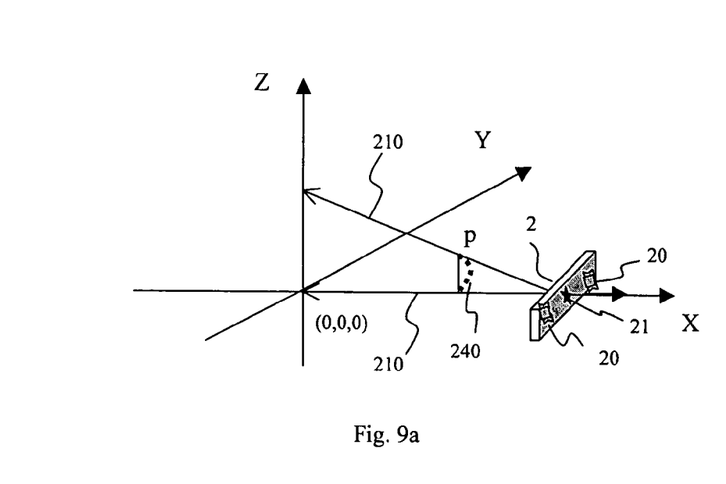
FIG. 9a is a front scan view.
Figure 9B:
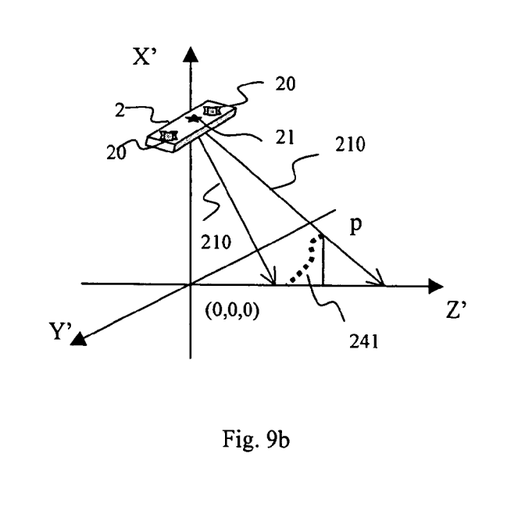
FIG. 9b is a top scan view.
Figure 9C:
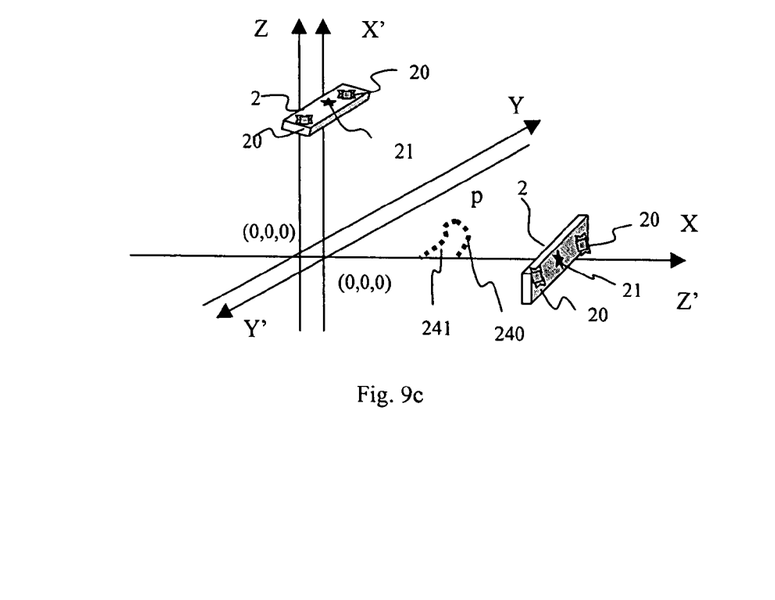
FIG. 9c is a perspective view with dual scan modules.

FIG. 9a shows a more detailed description of the front scan, where a straight line lighted by light source 21 results in a curve segment 240 seen by the image sensor 20, shown as a dotted curve. FIG. 9b shows a more detailed description of the top scan, where a dotted curve segment 241 is shown as seen by the image sensor 20. The final coordinates of the line-based object 4 are composed of both the front and the top surface line-based data, as shown by the dotted curve in FIG. 9c. Notice that the top scan data must be converted from X'-Y'-Z' system to that of X-Y-Z as shown in FIG. 9c. Again, the line lights 210 from the first and second scan modules 2 are aligned in one plane, so that there exists some overlap between the two sets of data. The principles of comparison and interpolation described earlier with reference to FIG. 8 can be applied to generate new combined data from these two independent line-based data as illustrated in FIG. 9c.

Figure 10:
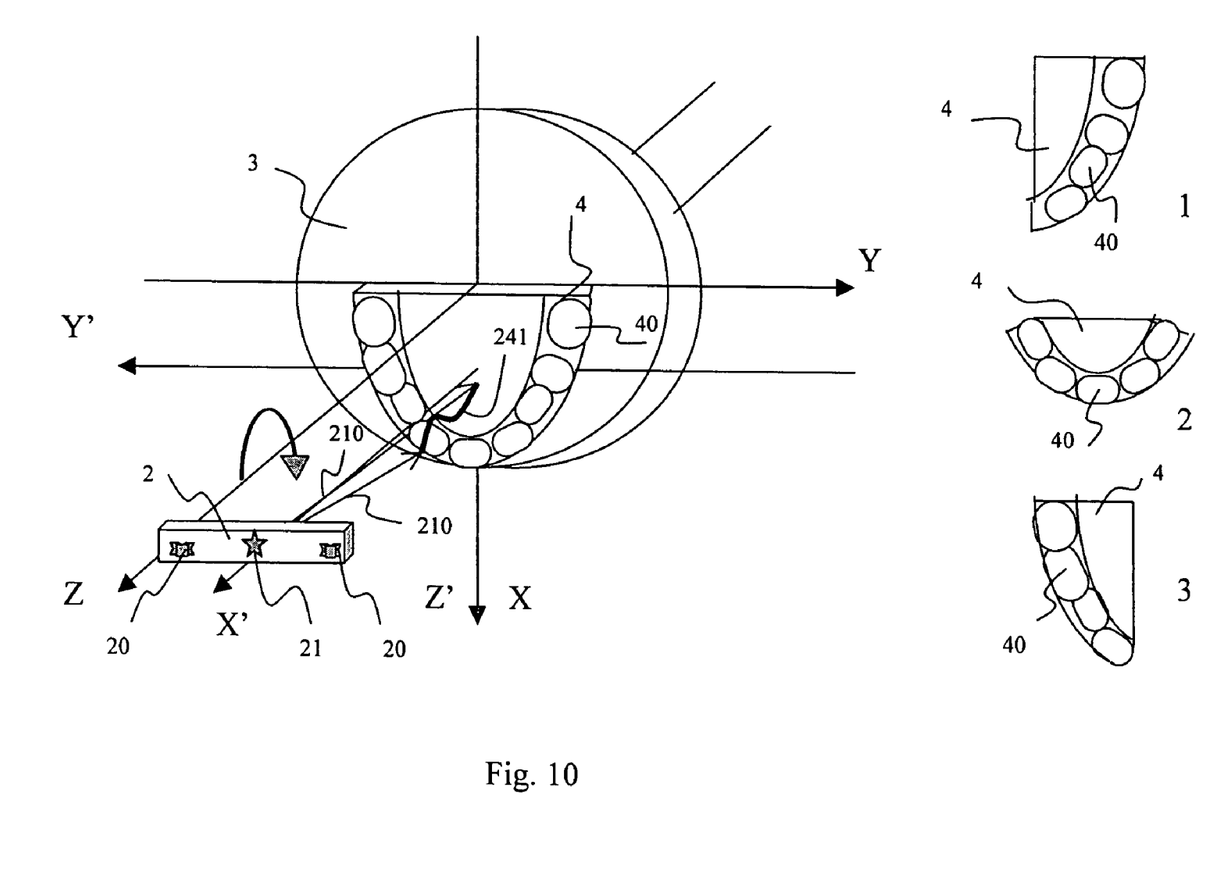
FIG. 10 illustrates a top surface scan on a tooth model.
Figure 11:
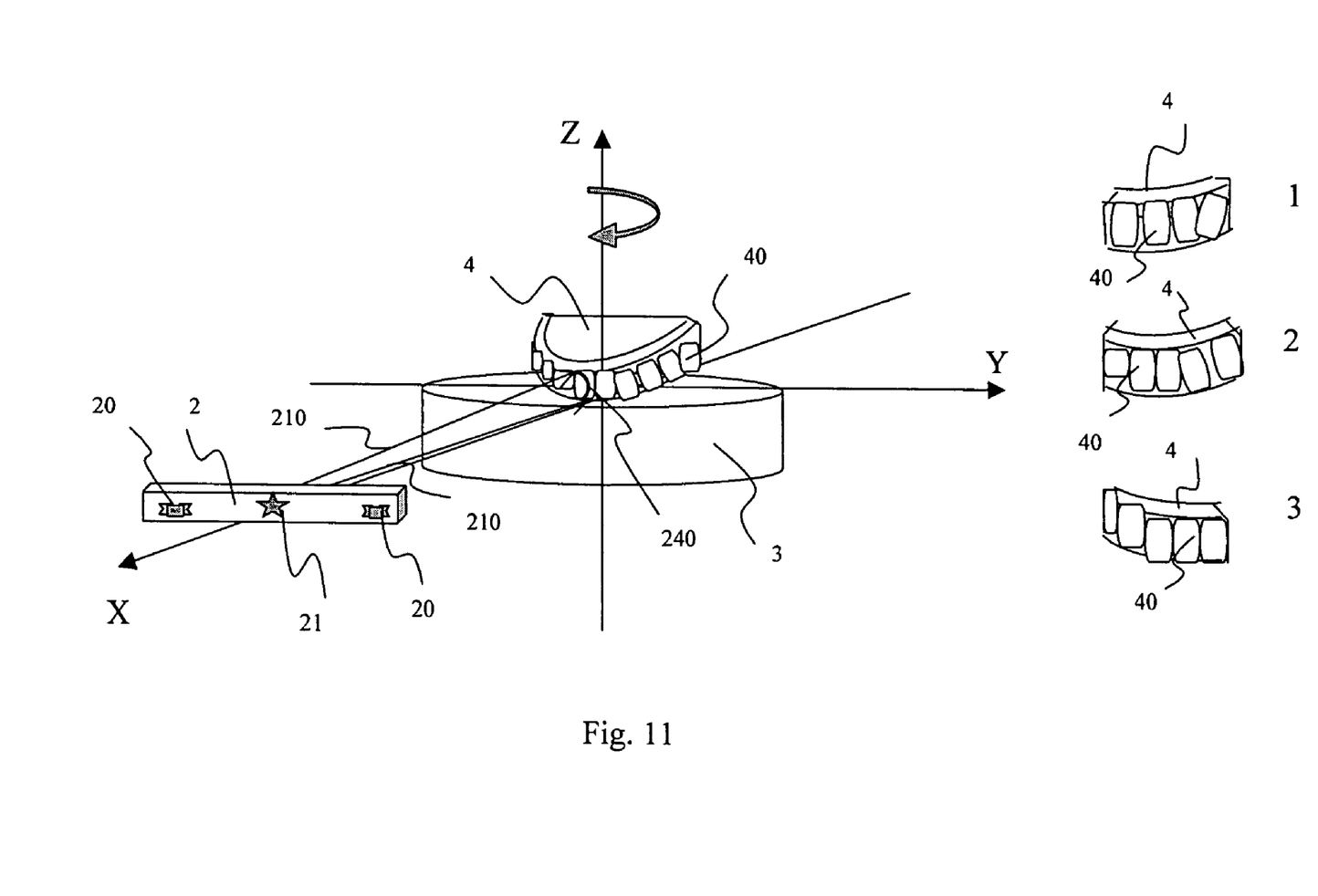
FIG. 11 shows a front surface scan on a tooth model.

The scanning of a tooth model is depicted in FIGS. 10 and 11. The top surface scan of the tooth model is shown in FIG. 10, and the front surface scan is depicted in FIG. 11. In FIG. 10, the line light source 21 generated by the top surface (second) scan module 2 lights only the positive side of the Z'-axis. (It is recommended that the light source 21 illuminates both + and −Z'-axis to cover both the inner and top surfaces of the tooth model.) As can be seen, the turntable 3 with tooth model 4 on it rotates in a clockwise direction. There are two coordinate systems, the X-Y-Z (for front scan) and X'-Y'-Z' (for top scan). The rotary table 3 rotates around the Z-axis. For the top (second) scan module 2, both the line light source 21 and the image sensors 20 are on the X'-Y' plane and are both facing the origin and Z'-axis. The image sensor 20 has a' angle with the X'-axis. For a point P', the height $z_0'$ and the distance from the origin $r_0'$ are computed using Equations 1 and 2. For better matching between the scanned object and the derived 3D top surface model, several 2D pictures can be taken to serve as references for color, texture, shape of tooth, and location of the narrow gaps between the teeth. Three 2D pictures, corresponding to right top surface, middle top surface, and left top surface of the tooth model are shown in FIG. 10.

FIG. 11 shows that the light source 21 and image sensors 20 are on the X-Y plane and are both directed toward the origin and the Z-axis. The image sensor 20 has an angle α relative to the X-axis. To better match the derived 3D front surface model with the scanned object, several 2D pictures are taken during the line scan as during the top scan. Similar to those in FIG. 10, only 3 2D pictures are displayed for illustration purposes. Equations 1 and 2 are used to compute the height $z_0$, and the distance from the origin $r_0$ of a point P. Both the front scan data and the top scan data are used to derive the final 3D tooth model.

It will be recognized by those skilled in the art that the same results can be obtained by allowing the rotary table 3 and tooth model 4 to remain stationary, with the two aligned scan modules 2 (light source 21 and image sensors 20) rotating. The frame of reference will be chosen by the user as a matter of convenience.

Figure 12:
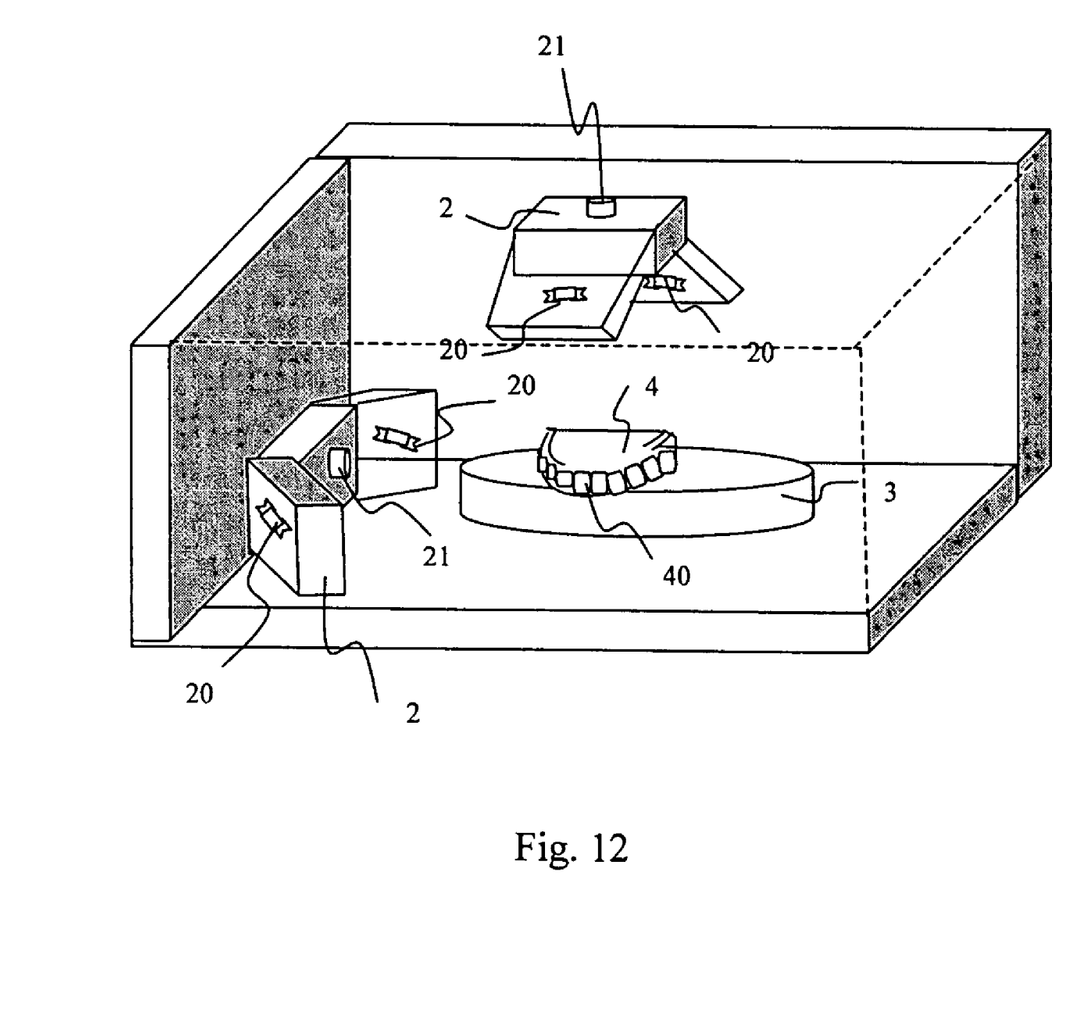
FIG. 12 is a perspective view of the apparatus used for a tooth model scan.

A preferred embodiment of a 3D surface scanning device adapted specifically for a tooth model is shown in FIG. 12. This setup consists of a turntable 3 and two scan modules 2 for the front and top surface scans respectively. The computer that is used to control the motion of the turntable 3, to compute the coordinates, and to display the 3D image of the object 4 is not shown. The parameters of the scan modules 2, such as the distance from the origin and the angle between image sensor 20 and light source 21, can be adjusted depending on the size of the object 4. Fixed distances and angles are illustrated in FIG. 12.

Figure 13:
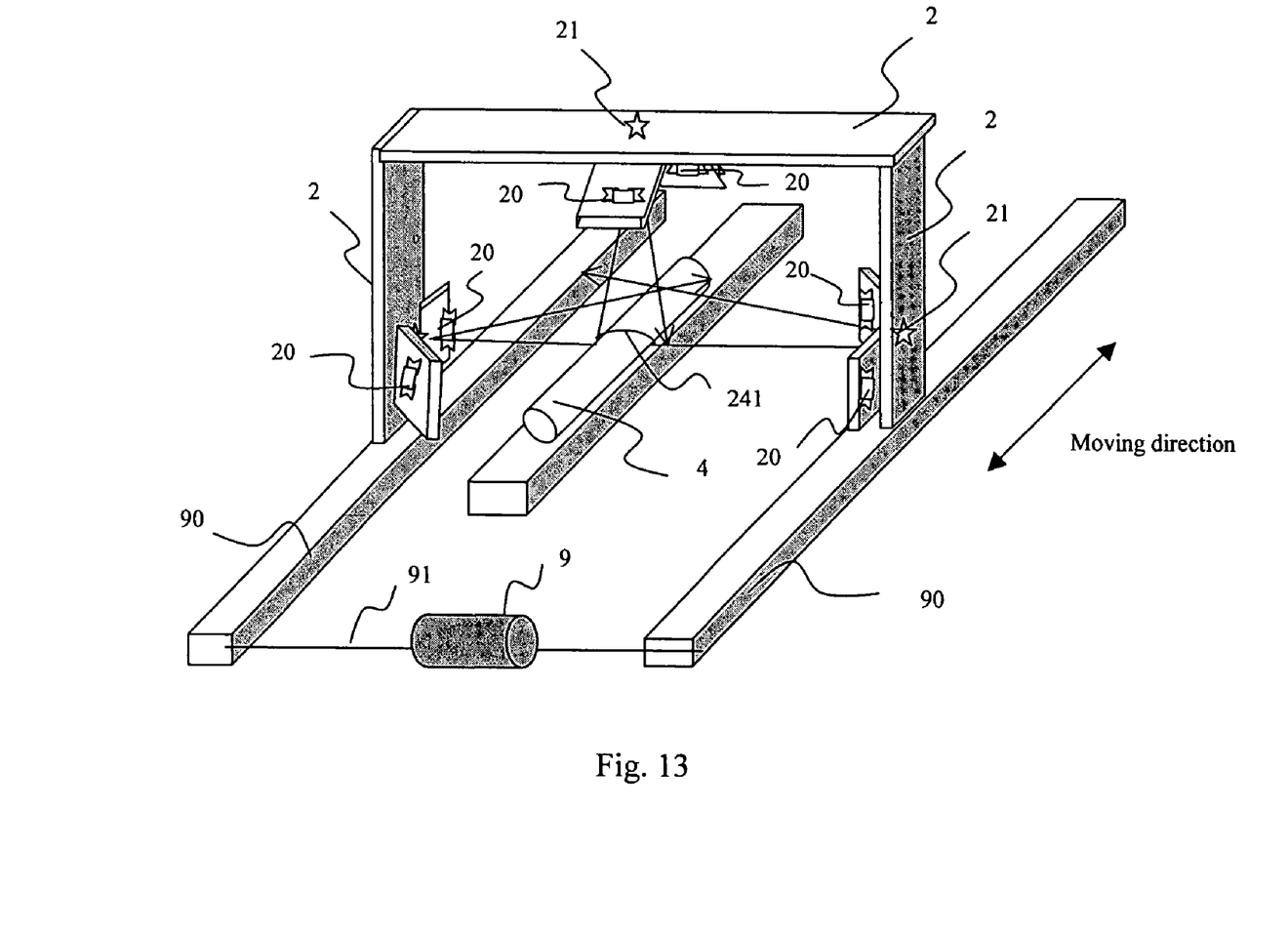
FIG. 13 is a perspective view of the apparatus set up for a general purpose scan.

Another embodiment of a general-purpose 3D scanner construction is depicted in FIG. 13. Three scan modules 2 are utilized in this embodiment; a first unit for a top scan, a second unit for a front scan, and a third unit for a back scan. Each of the scan modules 2 comprises a light source 21 (a laser line light generator) and two image sensors 20. In the embodiment illustrated, an aligned linear motion system is used to mount the scan modules 2. The linear motion system allows a much longer object to be scanned accurately.

The linear motion system comprises a rotary motor 9, a drive shaft 91, and a drive frame 90. The drive frame 90 serves as the vehicle to move the scan modules 2 as they scan the object 4. Drive shaft 91 rotates drive gears 92 that are meshed with teeth 93 affixed to the drive frame 90 so that drive frame 90 is moved linearly.

The parameters defined for the scan modules 2, such as the distance of the scan module 2 from the origin and the angle between the image sensors 20 and the light source 21, can be adjusted as required depending on the size of the scanned object 4. While a rack and pinion arrangement is shown in FIG. 13, it should be evident to those skilled in the art that any motion imparting arrangement could be utilized. The critical factor of the setup being the ability to move the scan modules 2 about the object to be scanned 4.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A method for determining the surface coordinates of an object, comprising the following steps:
   a) constructing a scanning apparatus comprising a plurality of scan modules and a motion device to move a subject object, each said scan module comprising a light source and at least two image sensors,
   b) deriving a set of mathematical equations to compute line-based surface coordinate data of said object from scanned line image values, said equations being independent of scanning speed,
   c) establishing a test pattern to calibrate said image sensors,
   d) scanning a subject object with said scanning apparatus
   e) merging scanning data from said at least two image sensors into a single line image data map for each scanning position of said motion device,
   f) aligning and merging multiple scanned line images to a single line-based coordinate data system,
   g) converting said line-based coordinate data to a 3D data map of said image.

2. The method for determining the surface coordinates of an object as defined in claim 1 wherein:
   said set of mathematical equations comprises equations to calculate surface coordinates of objects with portions of said object lying on multiple sides of a point of origin, said equations yielding cylindrical coordinates of a point as follows:
   $r_0 = L \cos \alpha - (L \sin \alpha)/\tan (\alpha+\beta)$ and $z_0 = (D-q)*b/D$;
   wherein L is a distance between a subject image sensor and an origin, $\alpha$ is an angle between said subject image sensor and said light source, angle $\beta$ is computed by $\tan \beta = a/L$, a is a horizontal distance of said point from a Z axis, b is a vertical distance of said point from an X-Y plane, $D = \operatorname{SQRT}(L^2+a^2)$, and $q = r_0 * \cos\alpha/\cos\beta$.

3. The method for determining the surface coordinates of an object as defined in claim 1 wherein:
   said set of mathematical equations comprises equations to calculate surface coordinates of objects with portions of said object lying on multiple sides of a point of origin, said equations yielding cylindrical coordinates of a point on a concave object as follows:
   $r_0 = -L*\cos \alpha + L*\sin \alpha/\tan (\alpha-\beta)$, and $z_0 = (q+D)*b/D$;
   wherein L is a distance between a subject image sensor and an origin, a is an angle between said subject image sensor and said light source, angle $\beta$ is computed by $\tan \beta = a/L$, a is a horizontal distance of said point from a Z axis, b is a vertical distance of said point from an X-Y plane, $D = \operatorname{SQRT}(L^2+a^2)$, and $q = r_0 * \cos\alpha/\cos \beta$.

4. An apparatus for scanning and collecting data on the surface of an object comprising:
   a moving device,
   at least two scan modules, each said scan module comprising at least one image sensor and a light source,
   a computing and control device; wherein
   said moving device imparts motion to said object relative to a frame which holds and moves the scan module or holds the object; and
   said computing and control device computes cylindrical coordinates of a point using a set of equations that are independent of scanning speed.

5. The apparatus for scanning and collecting data on the surface of an object as defined in claim 4 wherein:
   said light source is a stripe line light generator.

6. The apparatus for scanning and collecting data on the surface of an object as defined in claim 4 wherein:
   said light source produces a planar light emission, such as in a planar laser generator.

7. The apparatus for scanning and collecting data on the surface of an object as defined in claim 4 wherein:
   said computing and control device comprises a processor, a memory device, at least one input/output port, and a graphic display.

8. The apparatus for scanning and collecting data on the surface of an object as defined in claim 4 wherein:
   said computing and control device is a personal computer.

9. The apparatus for scanning and collecting data on the surface of an object as defined in claim 4 wherein:
   said computing and control device is a handheld PDA.

10. The apparatus for scanning and collecting data on the surface of an object as defined in claim 4 wherein:
    said image sensor is a CCD based camera.

11. The apparatus for scanning and collecting data on the surface of an object as defined in claim 4 wherein:
    said image sensor is a CMOS based camera.

* * * * *